United States Patent
Cachovan et al.

(10) Patent No.: US 11,065,475 B2
(45) Date of Patent: Jul. 20, 2021

(54) MULTI-CYCLE DOSIMETRY AND DOSE UNCERTAINTY ESTIMATION

(71) Applicant: Siemens Medical Solutions USA, Inc., Malvern, PA (US)

(72) Inventors: Michal Cachovan, Baiersdorf (DE); Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 473 days.

(21) Appl. No.: 16/207,661

(22) Filed: Dec. 3, 2018

(65) Prior Publication Data
US 2019/0168029 A1  Jun. 6, 2019

Related U.S. Application Data

(60) Provisional application No. 62/594,617, filed on Dec. 5, 2017.

(51) Int. Cl.
*A61N 5/10* (2006.01)
*A61B 6/03* (2006.01)

(52) U.S. Cl.
CPC ............ *A61N 5/1071* (2013.01); *A61B 6/037* (2013.01); *A61N 5/1039* (2013.01); *A61N 5/1001* (2013.01); *A61N 2005/1021* (2013.01); *A61N 2005/1052* (2013.01); *A61N 2005/1074* (2013.01)

(58) Field of Classification Search
CPC ............ A61N 5/1071; A61N 5/1039; A61N 2005/1052; A61N 2005/1074; A61N 5/1001; A61N 2005/1021; A61B 6/037
See application file for complete search history.

(56) References Cited

U.S. PATENT DOCUMENTS

| 8,350,222 B2 | 1/2013 | Vija et al. |
|---|---|---|
| 8,577,103 B2 | 11/2013 | Vija et al. |

(Continued)

FOREIGN PATENT DOCUMENTS

WO    2016/178115 A1    11/2016

OTHER PUBLICATIONS

Vija, A. Hans, White Paper, "Characteristics of the xSPECT reconstruction method", SPECT Research and Development, 2017, Order No. A91MI-10462-T1-7600, 24pp.

(Continued)

*Primary Examiner* — Marcus H Taningco

(57) ABSTRACT

A system and method include acquisition of a set of tomographic images of a patient volume associated with each of a plurality of timepoints of a first radiopharmaceutical therapy cycle, determination, for each of the plurality of timepoints, of a systematic uncertainty for each of a plurality of regions within the patient volume based on the set of tomographic images associated with the timepoint, determination, for each of the plurality of timepoints, of a quantitative statistical uncertainty based on the set of tomographic images associated with the timepoint, determination of a dose and a dose uncertainty for each of the plurality of regions based on the set of tomographic images, the systematic uncertainty and the quantitative statistical uncertainty for each of the plurality of timepoints, and display of a cumulative dose and cumulative dose uncertainty for each of the plurality of regions based on the dose and the dose uncertainty determined for each of the plurality of regions.

20 Claims, 9 Drawing Sheets

(56) References Cited

U.S. PATENT DOCUMENTS

| | | | |
|---|---|---|---|
| 8,675,936 B2 | 3/2014 | Vija et al. | |
| 9,171,353 B2 | 10/2015 | Vija et al. | |
| 9,332,907 B2 | 5/2016 | Vija | |
| 9,364,192 B2 * | 6/2016 | Vija | A61B 6/5258 |
| 2011/0299655 A1 * | 12/2011 | Takayama | A61B 6/032 |
| | | | 378/63 |
| 2016/0059039 A1 * | 3/2016 | Liu | A61N 5/1039 |
| | | | 600/1 |
| 2017/0105695 A1 | 4/2017 | Ma et al. | |
| 2017/0108596 A1 | 4/2017 | Ma et al. | |
| 2017/0119913 A1 * | 5/2017 | Osterkamp | A61K 47/68 |
| 2017/0193159 A1 | 7/2017 | Cachovan et al. | |
| 2017/0354333 A1 * | 12/2017 | Nishida | A61B 6/5217 |
| 2018/0061031 A1 | 3/2018 | Rong et al. | |

OTHER PUBLICATIONS

Cachovan, Michal "Motion Corrected Quantitative Imaging in Multimodal Emission Tomography", Erlangen, May 25, 2015, 144pp.

Vija, A. Hans, et al. "Quantitative SPECT for Time Activity Curve Estimation using Extra Modal Information for the Theranostics Application", published Sep. 12, 2016, 12pp.

Siegel, Jeffry A., et al. "MIRD pamphlet No. 16: techniques for quantitative radiopharmaceutical biodistribution data acquisition and analysis for use in human radiation dose estimates." Journal of Nuclear Medicine 40.2 (1999): 37S.

Dewaraja, Yuni K., et al. "MIRD pamphlet No. 23: quantitative SPECT for patient-specific 3-dimensional dosimetry in internal radionuclide therapy." Journal of nuclear medicine: official publication, Society of Nuclear Medicine 53.8 (2012): 1310.

Divoli, Antigoni, et al. "Effect of patient morphology on dosimetric calculations for internal irradiation as assessed by comparisons of Monte Carlo versus conventional methodologies." Journal of Nuclear Medicine 50.2 (2009): 316.

Stabin, Michael G., Richard B. Sparks, and Eric Crowe. "OLINDA/ EXM: the second-generation personal computer software for internal dose assessment in nuclear medicine." The Journal of Nuclear Medicine 46.6 (2005): 1023.

* cited by examiner

MULTI-CYCLE DOSIMETRY AND DOSE UNCERTAINTY ESTIMATION

CROSS-REFERENCE TO RELATED APPLICATIONS

The present application is related to and claims priority to U.S. Provisional Patent Application No. 62/594,617, filed Dec. 5, 2017, the contents of which are incorporated by reference in their entirety, for all purposes.

BACKGROUND

Conventional nuclear imaging begins with the introduction of a radiopharmaceutical into a patient volume. The radiopharmaceutical emits gamma rays (in the case of single-photon-emission-computer-tomography (SPECT) imaging) or positrons which annihilate with electrons to produce gamma rays (in the case of positron-emission-tomography (PET) imaging). A detector system located outside the volume detects the emitted gamma rays and reconstructs images based thereon. The images may be used to diagnose pathology within the patient volume.

According to theranostics, the radiopharmaceutical is used as a therapeutic agent as well as a source of diagnostic data. Specifically, radiation emitted by the radiopharmaceutical is intended to apply a therapeutic dose to targeted tissue within the volume. Multi-cycle theranostics involves the introduction of tissue-dosing radiopharmaceuticals at multiple successive procedures (i.e., cycles) occurring at different times (typically different days). Nuclear images are acquired at multiple timepoints after each cycle in order to monitor the distribution and amount of dose over time.

It is desirable to estimate the dose delivered to tissue by the introduced radiopharmaceutical. Conventional acquisition, reconstruction and dosimetry techniques are unable to provide accurate dose estimations, particularly cumulative dose estimations over multiple cycles. Consequently, extremely conservative doses are applied to ensure that undue tissue damage does not occur.

Efficient techniques to accurately estimate patient-specific dosimetry and dose uncertainty, per cycle and overall, are desired. Accurate estimations may allow for more aggressive therapy planning, and may facilitate modification of a therapy plan between cycles in a case that an actually-delivered dose to-date differs from a planned dose.

DETAILED DESCRIPTION

The following description is provided to enable any person in the art to make and use the described embodiments and sets forth the best mode contemplated for carrying out the described embodiments. Various modifications, however, will remain apparent to those in the art.

Generally, some embodiments provide a workflow to efficiently and accurately estimate cumulative patient-specific dosimetry and dose uncertainty throughout delivery of multi-cycle radiopharmaceutical therapy. Embodiments may also be used in conjunction with other therapy types, such as external beam therapy, in which imaging is used to perform therapy planning and monitoring to assess dose distribution of an underlying therapeutic agent.

More particularly, and as a brief introduction, some embodiments estimate systematic uncertainty at the organ level and voxel level for each imaging timepoint of a theranostic cycle, and also estimate spatial quantitative statistical uncertainty for each timepoint. Examples of systematic uncertainty determination include but are not limited to partial volume corrections, attenuation corrections, scatter corrections, motion corrections, and system model corrections.

Dose and dose uncertainty are determined for each organ and voxel based on the corresponding systematic uncertainties and quantitative statistical uncertainties, and a cumulative dose and dose uncertainty are determined for each organ and voxel. The cumulative and per-cycle dose and dose uncertainty may be presented in order to facilitate monitoring and/or modification of therapy.

Figure 1:
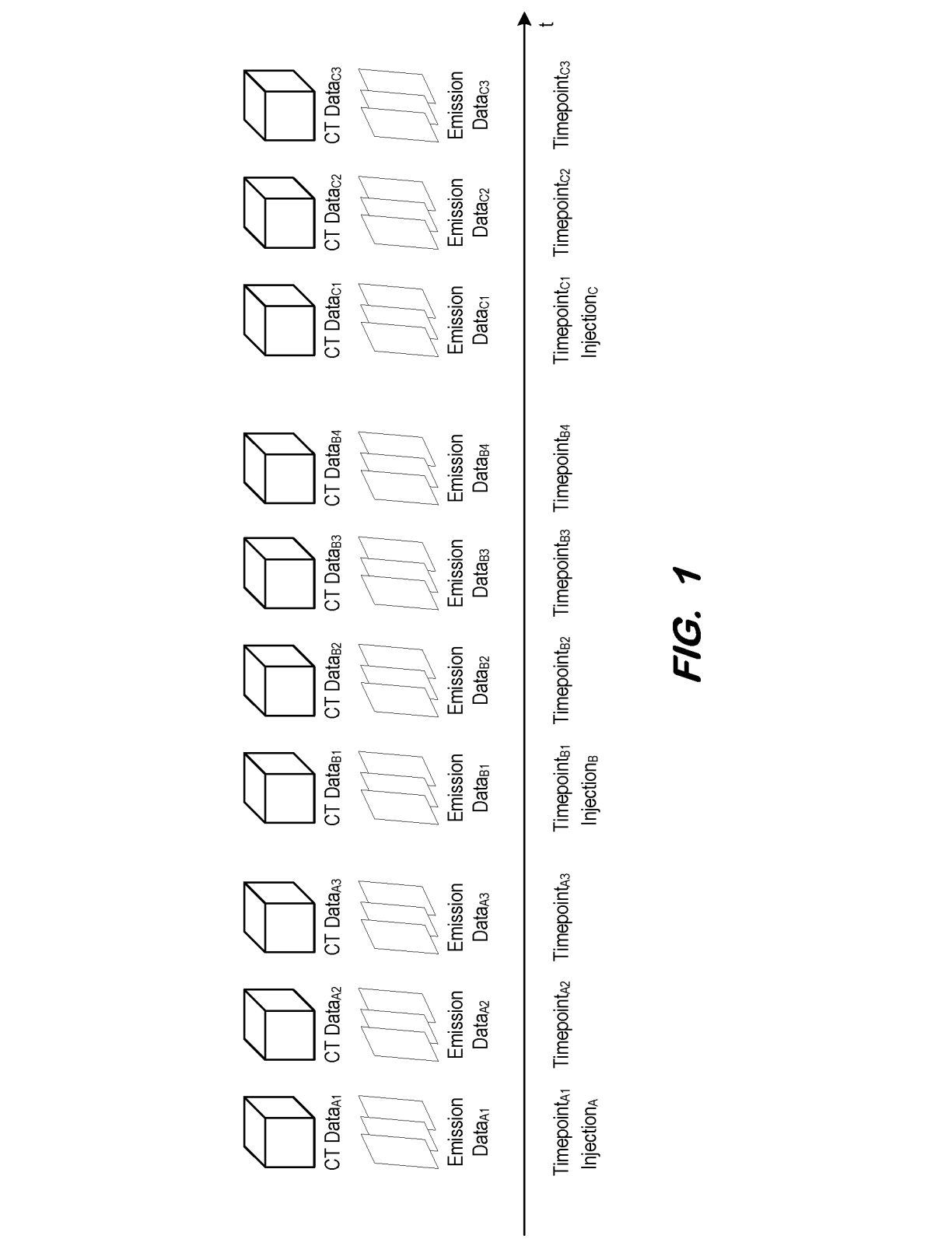
FIG. 1 illustrates multi-cycle theranostics according to some embodiments.

FIG. 1 illustrates a theranostics process according to some embodiments. The illustrated process includes three cycles spaced over a number of days. Embodiments are not limited to any particular number of cycles, or to any particular time period between cycles.

Each cycle includes an injection of radiopharmaceutical at a first timepoint and acquisition of images at several subsequent timepoints. Any suitable therapeutic radiopharmaceutical may be employed, and may be introduced into a patient volume via injection, ingestion, and/or any other suitable means. Moreover, the number of imaging timepoints is not limited to any particular number and need not be the same for each cycle.

According to the illustrated example, tomographic nuclear emission data and computed tomography data are acquired at each timepoint. Emission data may comprise a plurality of sets of two-dimensional emission data generated by an emission imaging system during a scan of a body. As described above, such a system may comprise a SPECT system, a PET system, or another type of nuclear imaging system that is or becomes known.

In some embodiments, computed tomography data is not acquired at each timepoint. The processes described herein may use computed tomography data from a prior a study or computed tomography data which is acquired once per cycle, for example.

Embodiments are not limited to the two imaging modalities of FIG. 1, or to only two modalities. Embodiments may include acquisition of tomographic SPECT data and magnetic resonance (MR) data at each timepoint, for example.

Figure 2:
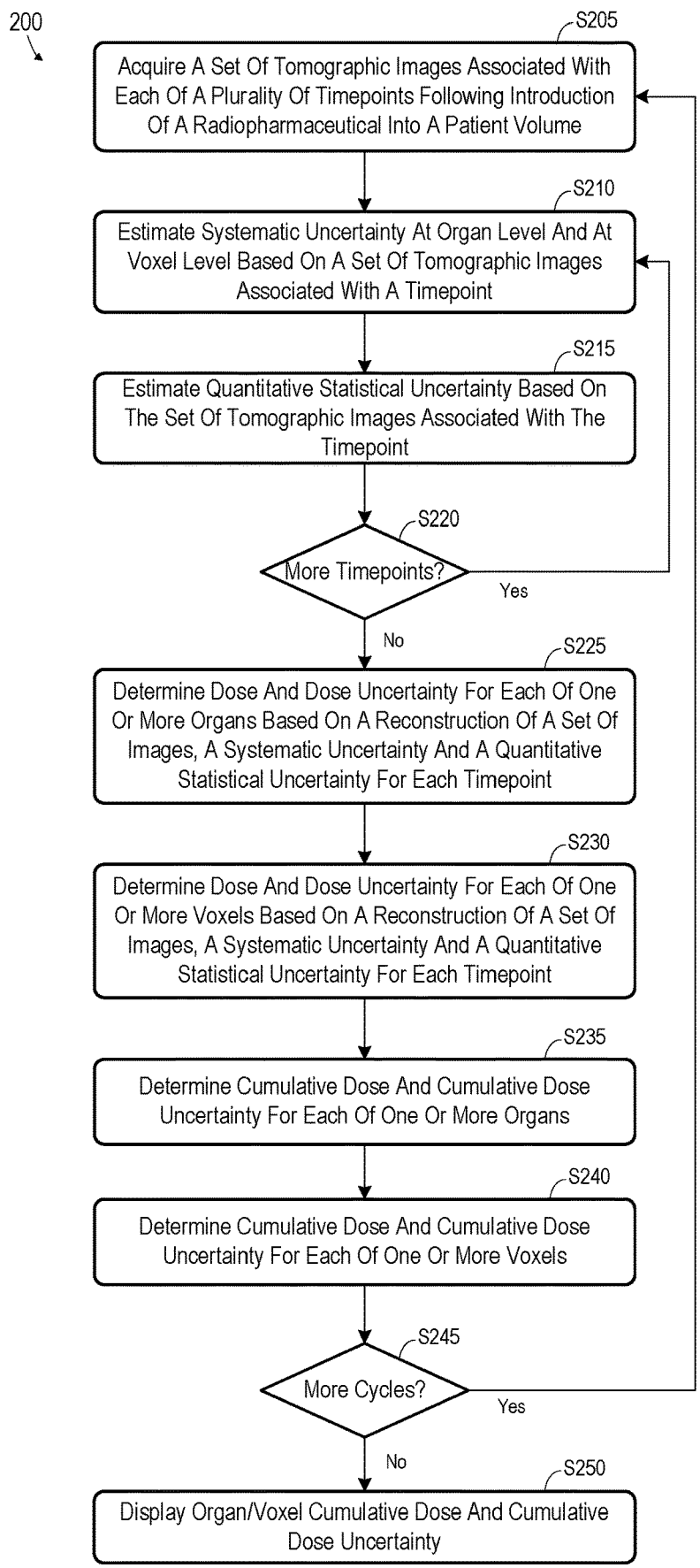
FIG. 2 is a flow diagram of a process according to some embodiments.

FIG. 2 is a flow diagram of process 200 according to some embodiments. Process 200 and the other processes described herein may be performed using any suitable combination of hardware and software. Software program code embodying these processes may be stored by any non-transitory tangible medium, including but not limited to a fixed disk, a volatile or non-volatile random access memory, a DVD, or a Flash drive. Embodiments are not limited to the examples described below.

Initially, at S205, a set of tomographic images is acquired for each of a plurality of timepoints. The timepoints follow introduction of a radiopharmaceutical into a patient volume depicted in the tomographic images. For example, prior to S205, a radiopharmaceutical is introduced into a patient volume (e.g., at $Timepoint_{A1}$ of FIG. 1) and a plurality of sets of emission data are acquired (e.g., at $Timepoint_{A1}$, $Timepoint_{A2}$, $Timepoint_{A3}$, $Timepoint_{A4}$ of FIG. 1). The amount and location of the introduced radiopharmaceutical may be dictated by a predetermined radiotherapy plan.

Figure 3:
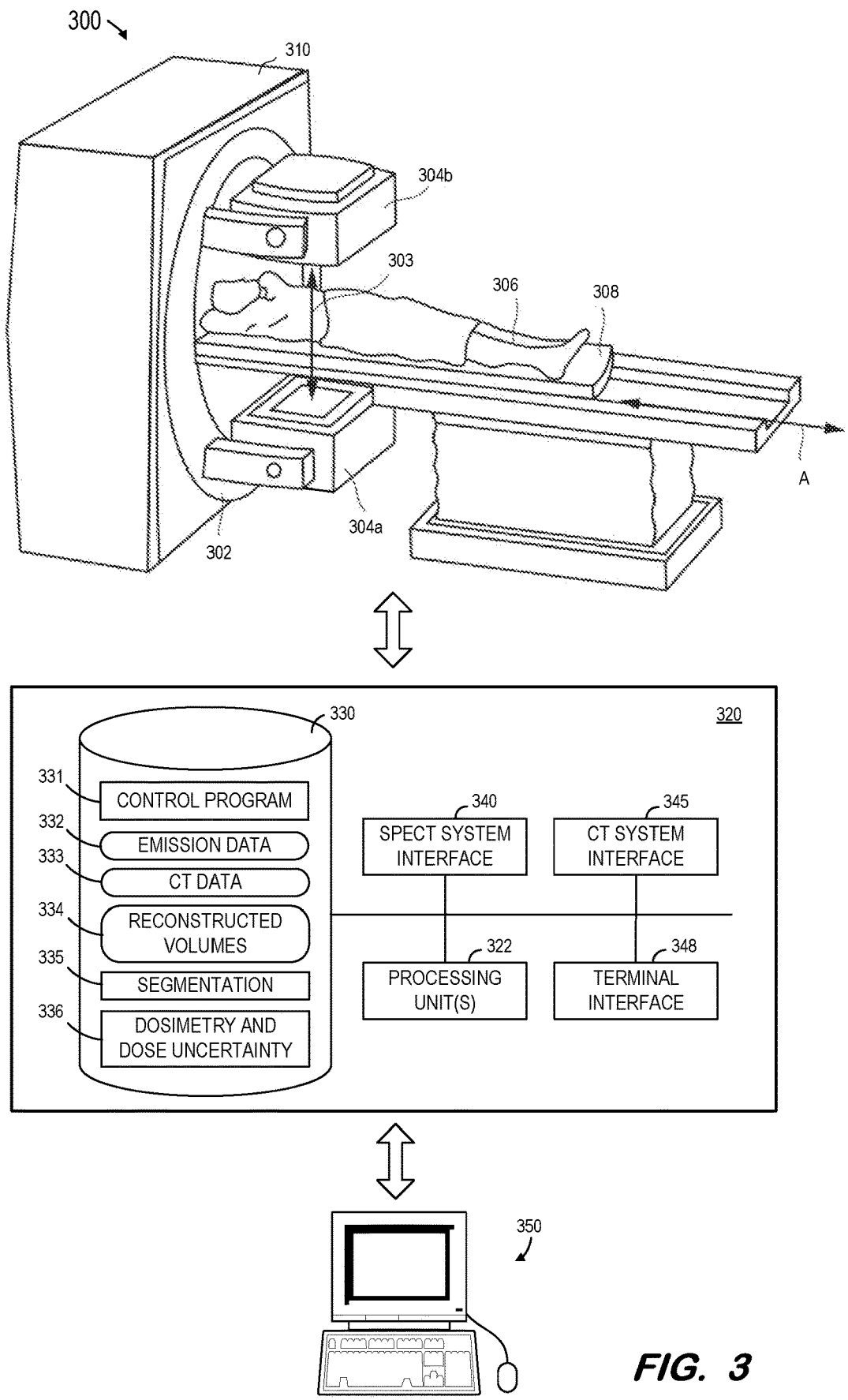
FIG. 3 is a block diagram of a system to perform imaging and dosimetry estimations according to some embodiments.

FIG. 3 illustrates SPECT-CT system 300 to execute process 200 according to some embodiments. According to some embodiments, an imaging system performs S205 to acquire imaging data and a separate computing system performs the remainder of process 200.

System 300 includes gantry 302 to which two or more gamma cameras 304a, 304b are attached, although any number of gamma cameras can be used. A detector within each gamma camera detects gamma photons (i.e., emission data) emitted by a radiopharmaceutical within the body of patient 306 lying on a bed 308. Bed 308 is slidable along axis-of-motion A. At respective bed positions (i.e., imaging positions), a portion of the body of patient 306 is positioned between gamma cameras 304a, 304b in order to capture emission data from that body portion.

System 300 also includes CT housing 310 including an X-ray imaging system (unshown) as is known in the art. Generally, and according to some embodiments, the X-ray imaging system acquires two-dimensional X-ray images of patient 306 before, during and/or after acquisition of emission data 303 using gamma cameras 304a and 304b.

Control system 320 may comprise any general-purpose or dedicated computing system. Accordingly, control system 320 includes one or more processing units 322 configured to execute processor-executable program code to cause system 320 to operate as described herein, and storage device 330 for storing the program code. Storage device 330 may comprise one or more fixed disks, solid-state random access memory, and/or removable media (e.g., a thumb drive) mounted in a corresponding interface (e.g., a USB port).

Storage device 330 stores program code of system control program 331. One or more processing units 322 may execute system control program 331 to, in conjunction with SPECT system interface 340, control motors, servos, and encoders to cause gamma cameras 304a, 304b to rotate along gantry 302 and to acquire two-dimensional emission data 303 at defined imaging positions during the rotation. The acquired emission data 332 may be stored in storage device 330.

One or more processing units 322 may also execute system control program 331 to, in conjunction with CT system interface 345, cause a radiation source within CT housing 310 to emit radiation toward body 306 from different projection angles, to control a corresponding detector to acquire two-dimensional CT images, and to reconstruct three-dimensional CT images from the acquired images. The CT images may be acquired substantially contemporaneously with the emission data at given timepoints as described herein, and the reconstructed images may be stored as CT data 333.

Control program 331 may be further executed to reconstruct reconstructed volumes 334 based on emission data 332 and CT data 333 as is known. For example, a mu-map may be determined based on a set of CT data 333 and used to reconstruct a volume 334 from a corresponding set of emission data 332. Storage device 330 also includes processor-executable process steps to perform segmentation 335 and determine dosimetry and dose uncertainty 336 according to some embodiments.

Control system 320 may transmit visual representations of per-organ and per-voxel dosimetry and dose uncertainty to terminal 350 via terminal interface 348. The visual representations may be cumulative or per-theranostic cycle. Terminal 350 may comprise a display device and an input device coupled to system 320. Terminal 350 may receive user input for controlling display of the representations, operation of imaging system 300, and/or the processing described herein. In some embodiments, terminal 350 is a separate computing device such as, but not limited to, a desktop computer, a laptop computer, a tablet computer, and a smartphone.

Each of component of system 300 may include other elements which are necessary for the operation thereof, as well as additional elements for providing functions other than those described herein.

Embodiments are not limited to a SPECT imaging system and/or a CT imaging system as described above. For example, embodiments may employ any other imaging modalities (e.g., a magnetic resonance scanner, a positron-emission scanner, etc.) for acquiring image data.

Returning to process 200, S210 includes estimation of a systematic uncertainty at the organ level and at the voxel level based on a set of tomographic images associated with a timepoint (e.g., $Timepoint_{A1}$). The systematic uncertainty may comprise any one or more systematic uncertainties as is known in the art. An example will be provided herein with respect to systematic uncertainties caused by the partial volume effect.

Figure 4:
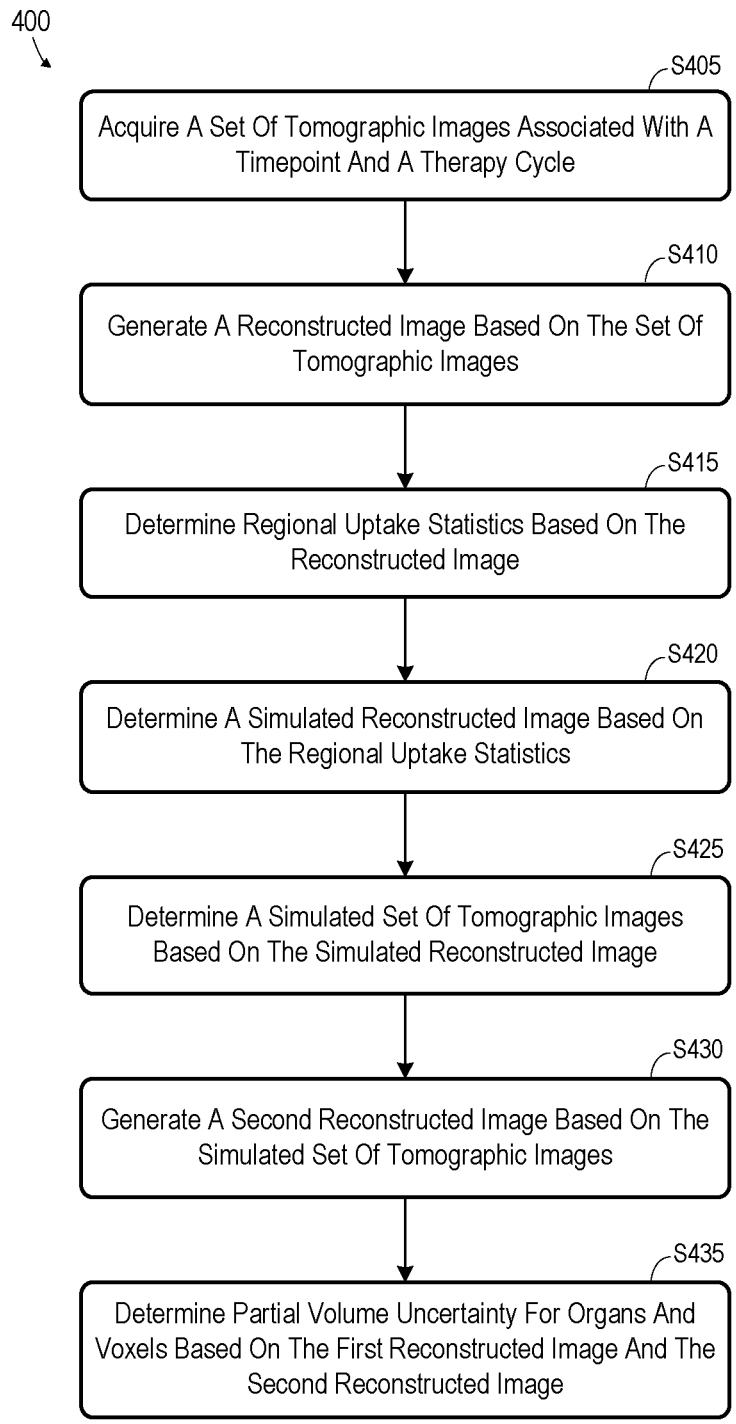
FIG. 4 is a flow diagram of a process to estimate systematic uncertainty due to partial volume effects according to some embodiments.

As is known, the partial volume effect causes the measured uptake activity as represented in a reconstructed volume to be less than the actual activity for small volumes (e.g., volumes with linear dimensions less than ~3× the full width half maximum (FWHM) of the effective point spread function (PSF) of the detector (i.e., the emission tomography imaging system). Discretization may also cause edge voxels to involve a mix of different tissues. Therefore, also due to the partial volume effect, the reconstructed activity concentration near edges of organs or other objects may be lower than the actual activity concentration. Examples of S210 according to some embodiments will be described with respect to FIGS. 4 and 5.

S215 includes estimation of quantitative statistical uncertainty based on the set of tomographic images associated with the present timepoint. The estimated quantitative statistical uncertainty is a spatial measure of uncertainty in uptake activity due to acquisition system noise. Examples of S215 according to some embodiments will be described with respect to FIGS. 6 and 7.

At S220, it is determined whether additional timepoints for the current cycle exist. If so, flow returns to S205 and continues as described above to calculate a systematic uncertainty and a quantitative statistical uncertainty for a next timepoint. Flow continues in this manner until a systematic uncertainty and a quantitative statistical uncertainty have been determined for each timepoint of a theranostic cycle.

Next, at S225, a dose and a dose uncertainty are determined for each of one or more organs. The determination is based on a tomographic reconstruction, a systematic uncertainty, and a quantitative statistical uncertainty for each timepoint. As will be described in more detail with respect to FIGS. 8 and 9, S225 may comprise determination of uptake values and uptake value uncertainties for each organ at each timepoint, and determination of a residence time and residence time uncertainty associated with each organ based on the uptake values and uptake value uncertainties. The dose and dose uncertainty for an organ may then be estimated based on the residence time and residence time uncertainty for the organ.

S230 may proceed similarly to S225, but at the voxel level. For instance, a dose and a dose uncertainty are determined for each of one or more voxels based on a tomographic reconstruction, a systematic uncertainty, and a quantitative statistical uncertainty for each timepoint.

A cumulative dose and dose uncertainty for each organ is determined at S235 based on the dose and dose uncertainty determined for the organ at S225 and on any cumulative dose and dose uncertainty which was previously-determined for the organ based on prior cycles of the current multi-cycle therapy. Similarly, a cumulative dose and dose uncertainty for each voxel is determined at S240 based on the dose and dose uncertainty determined for the voxel at S230 and on any previously-determined cumulative dose and dose uncertainty.

The above description of process 200 relates to a single cycle. At S245, it is determined whether additional cycles have been executed. If so, flow returns to S205 and continues to determine a per-organ and per-voxel dose and dose uncertainty associated with a next cycle, and a cumulative per-organ and per-voxel dose and dose uncertainty over all prior cycles.

The per-organ and/or per-voxel cumulative dose and cumulative dose uncertainty is displayed at S250. According to some embodiments, an operator may request display of a dose and dose uncertainty associated with any particular cycle, or a cumulative dose and cumulative dose uncertainty representing any 1 through n cycles of a multi-cycle therapy plan.

Figure 5:
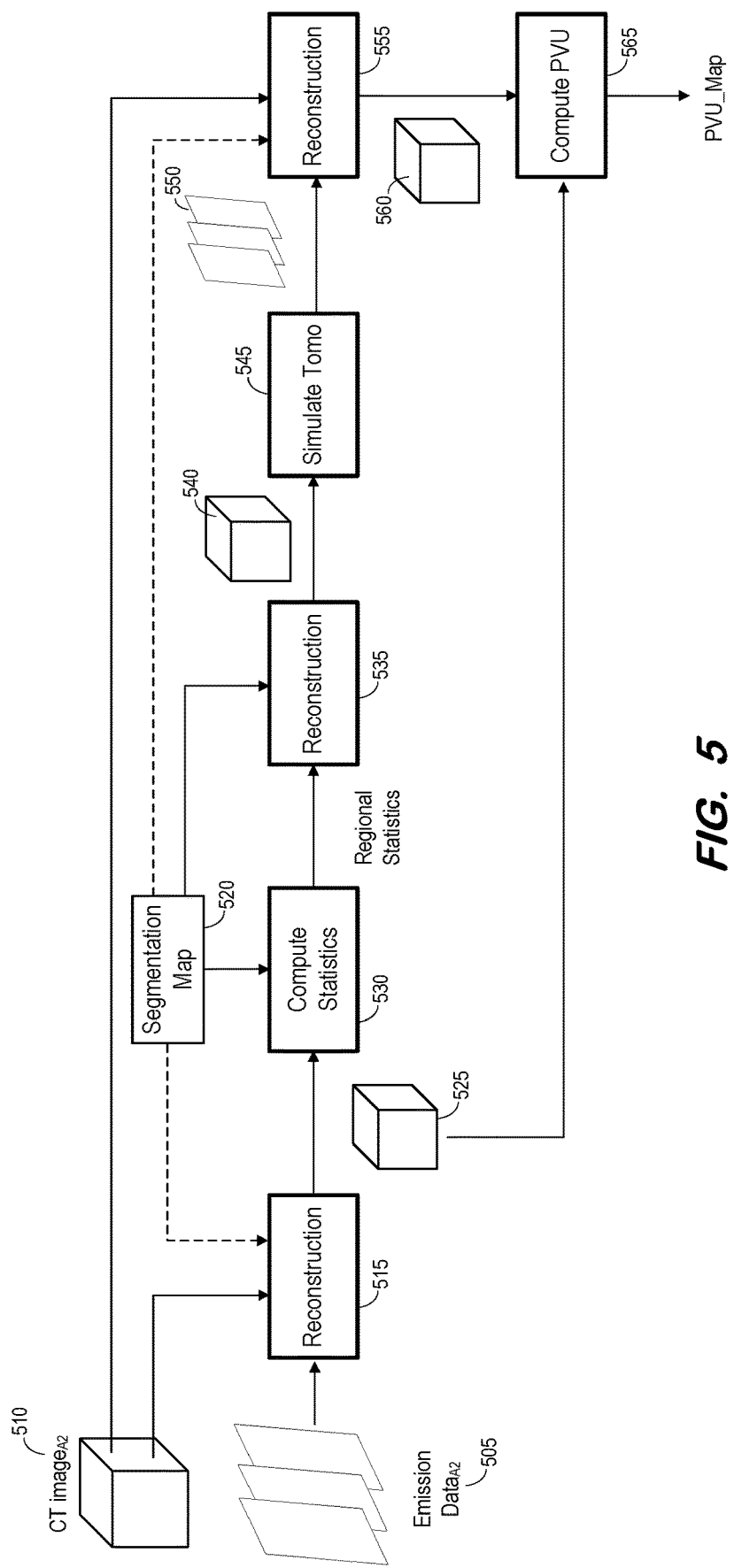
FIG. 5 is a block diagram illustrating estimation of systematic uncertainty due to partial volume effects according to some embodiments.

As mentioned above, FIGS. 4 and 5 depict estimation of uncertainty caused by the partial volume effect and associated with a timepoint within a therapy cycle according to some embodiments. S405 of process 400 includes acquisition of a set of tomographic images associated with a timepoint and a therapy cycle. As shown in FIG. 5, S405 may include acquisition of emission data 505 associated with Timepoint$_{A2}$ of FIG. 1. FIG. 5 also shows CT image$_{A2}$ 510 which may also be acquired at S405 and Timepoint$_{A2}$ according to some embodiments.

A reconstructed image is generated based on the acquired set of tomographic images at S410. FIG. 5 depicts the generation of reconstructed image 525 by reconstruction component 515 based on emission data 505 and CT image$_{A2}$ 510. For example, a mu-map may be generated based on CT image 510 and used to reconstruct image 525 from emission data$_{A2}$ 505. The reconstruction at S410 may utilize any reconstruction technique and/or algorithms which are or become known. Non-exhaustive examples of such techniques/algorithms are set forth in U.S. Pat. Nos. 8,350,222, 8,577,103, 8,675,936, 9,171,353, and 9,332,907.

Reconstruction component 515 may use segmentation map 520 to assist the reconstruction process. As is known, segmentation map 520 may be generated based on previously-acquired images of one or more imaging modalities (e.g., CT, SPECT, MR) in order to define regions of the patient volume. The defined regions may include organs, extremities, anatomical structures, gray matter, white matter, tumors, etc.

Next, at S415, uptake statistics are determined for various regions of the patient volume based on the reconstructed image. The uptake statistics may provide an indication of the radiation emissions within various regions as represented within the reconstructed image. FIG. 5 shows the generation of regional statistics by compute statistics component 530 based on segmentation map 520 and reconstructed image 525.

A further reconstruction occurs at S420 based on the regional statistics. The reconstruction at S420 may employ the same or different techniques as those used to generate the reconstructed image at S410. In the example of FIG. 5, reconstruction component 535 generates "simulated" reconstructed image 540 based on the regional statistics generated by component 530 and on segmentation map 520.

A simulated set of tomographic images is determined based on the simulated reconstructed image at S425. Determination of the simulated set of tomographic images may be based on a Monte Carlo simulation, a data model, or other technique. With reference to FIG. 5, component 545 generates simulated tomographic images 550 based on simulated image 540.

Another volume is reconstructed based on the simulated images at S430. Again, the reconstruction at S430 may proceed using the same or different techniques which were used for the prior reconstructions of process 400. As indicated by a dotted line of FIG. 5, reconstruction component 555 may employ previously-used segmentation map 520 to generate reconstructed image 560 according to some embodiments of S430.

A partial volume uncertainty is computed for one or more organs and one or more voxels of the patient volume at S435. With reference to FIG. 5, compute component 565 may compute the partial volume uncertainty based on differences between the uptake statistics of reconstructed image 525 and of reconstructed image 560. Segmentation map 520 may be used to generate a partial volume uncertainty map of the differences, per voxel and/or per organ.

Figure 6:
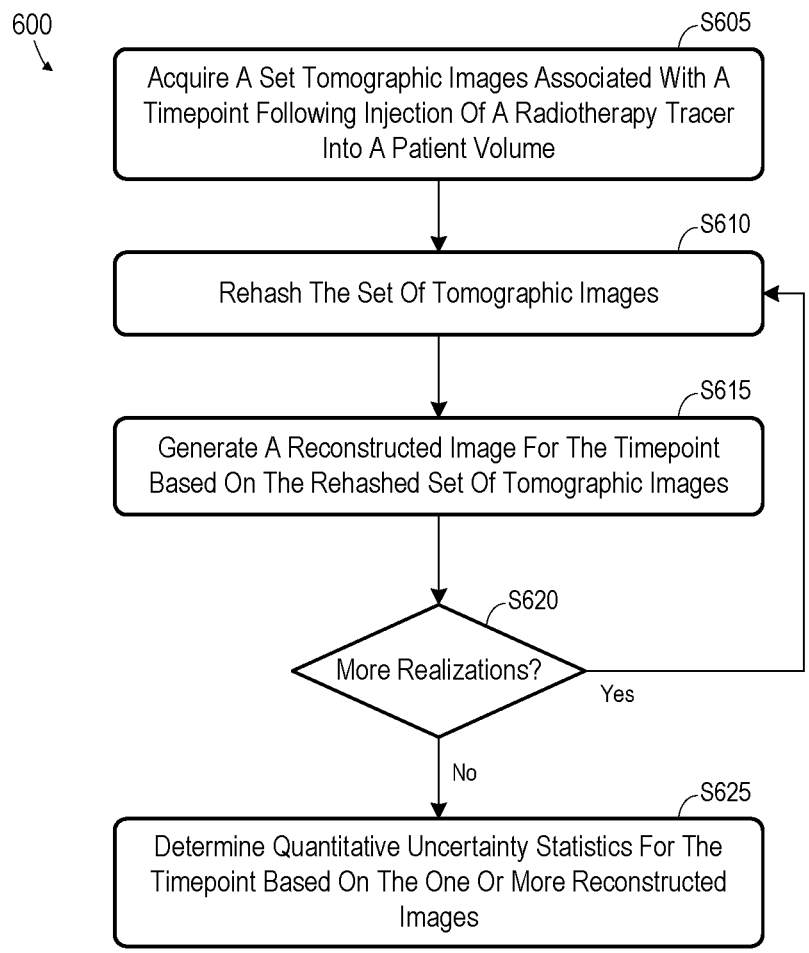
FIG. 6 is a flow diagram of a process to estimate quantitative statistical uncertainty according to some embodiments.
Figure 7:
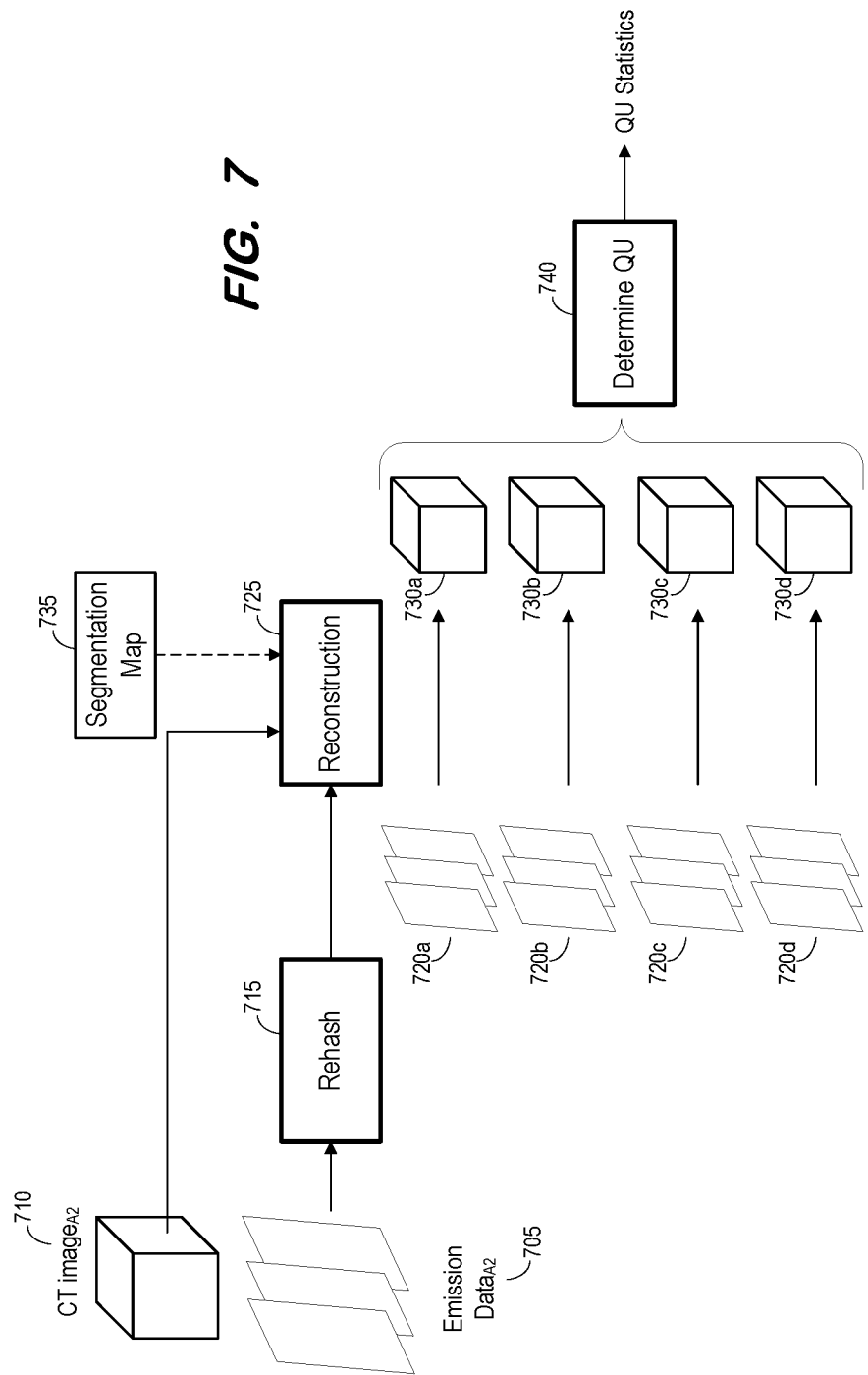
FIG. 7 is a block diagram illustrating quantitative statistical uncertainty estimation according to some embodiments.

FIGS. 6 and 7 depict estimation of quantitative statistical uncertainty associated with a timepoint within a therapy cycle according to some embodiments. As described with respect to S405, S605 of process 600 includes acquisition of a set of tomographic images associated with a timepoint and a therapy cycle. FIG. 7 shows emission data$_{A2}$ 705 and CT image$_{A2}$ 710 associated with Timepoint$_{A2}$ of FIG. 1 and acquired at S605 according to some embodiments.

At S610, the set of tomographic images is rehashed using any rehashing technique known in the art. For example, Poisson-distributed data can be rehashed using a Poisson random number generator which creates n pseudo-observations from a Poisson distribution with a defined lambda (i.e., the average number of events detected). Accordingly, S610 may include generation of a Poisson rehash of the set of tomographic images. In the FIG. 7 example, rehash component 715 generates rehashed images 720a based on emission data 705.

A reconstructed image is generated from the rehashed set of tomographic images at S615. The reconstruction may utilize any reconstruction technique, and, as shown in FIG.

7, may utilize a CT image (i.e., CT image$_{42}$ 710) associated with the original set of tomographic images and a segmentation map (i.e., segmentation map 735). The segmentation map may be used as extra modal information to drive application-dependent emission recovery.

At S620 it is determined whether additional realizations of the set of tomographic images are to be created. For example, some embodiments may be designed to generate ten reconstructed images based on ten different rehashed sets of tomographic images. In such a case, flow returns from S620 to S610 if all ten realizations have not yet been generated.

Upon returning to S610, the initially-acquired set of images is again rehashed (again using a Poisson random number generator), and another reconstructed image is generated based on the rehashed images at S615. For example, at a second iteration of S610 and S615, images 720*b* are generated by rehash component 715 and image 730*b* is reconstructed therefrom by reconstruction component 725. FIG. 7 illustrates four iterations of S610 and S615, resulting in images 730*a-d*. It should be noted that the multiple rehashings and corresponding reconstructions may be performed in parallel according to some embodiments.

Flow proceeds from S620 to S625 if all realizations have been generated. At S625, quantitative uncertainty statistics per organ and per voxel for the timepoint are determined based on the one or more reconstructed images. With reference to FIG. 7, quantitative uncertainty statistics 740 for Timepoint$_{42}$ are determined based on images 730*a-d*. For example, a mean, standard deviation and percentage uncertainty may be determined based on images 730*a-d*. Since the noise of each reconstructed image may be uncorrelated to the signal, the locations of signal and noise may be determined via comparison of images 730*a-d*.

Figure 8:
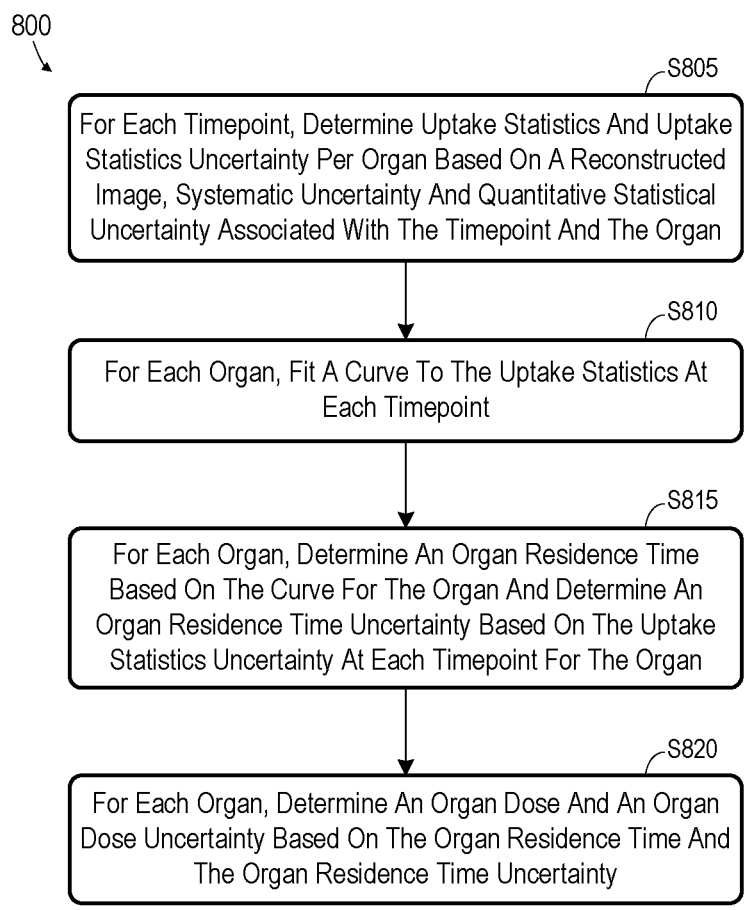
FIG. 8 is a flow diagram of a process to determine dose and dose uncertainty for each of one or more organs according to some embodiments.

FIG. 8 illustrates process 800 according to some embodiments. Process 800 may comprise an implementation of S225 of process 200, for example. Accordingly, process 800 may be performed to determine, for a given timepoint, a dose and a dose uncertainty for each of one or more organs based on a reconstruction of a set of images, a systematic uncertainty and a quantitative statistical uncertainty. S230 may also proceed similarly to process 800, although with respect to one or more voxels rather than organs.

At S805, uptake statistics and uptake statistics uncertainties per organ are determined for each timepoint of a therapy cycle. The statistics and uncertainties are determined based on a reconstructed image, a systematic uncertainty and a quantitative statistical uncertainty associated with the timepoint and organ. As described with respect to process 200, a reconstructed image, a per organ systematic uncertainty and a per organ quantitative statistical uncertainty are determined for each timepoint by virtue of S205, S210 and S215. These values are used at S805 to determine uptake statistics and uptake statistics uncertainty per organ for each timepoint. The determination at S805 may also employ a segmentation map associated with the timepoint and previously-determined as described above.

Figure 9:
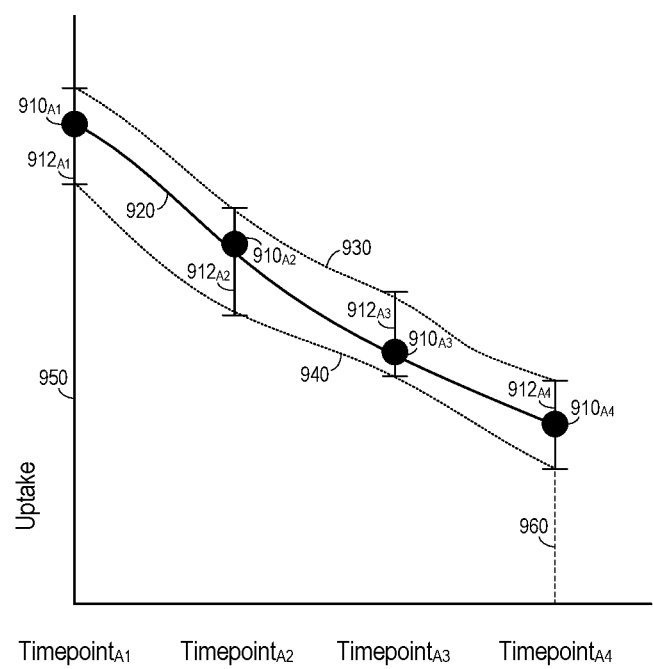
FIG. 9 is a graph illustrating uptake activity, and uptake activity uncertainty according to some embodiments.

At S810, and for each organ, a curve is fit to the uptake statistics at each timepoint. FIG. 9 illustrates curve fitting of the uptake statistics for one organ according to some embodiments. The uptake statistics for each of Timepoints$_{41-44}$ are graphed as points 910$_{41-44}$. The uptake statistics uncertainties for each timepoint are graphed as uncertainty bars 912$_{41-44}$. Curve 920 is determined to fit to the uptake statistics and may comprise a function of any suitable order. Also shown are curves 930 and 940 which are fit to the upper and lower bounds of the uptake statistics uncertainties, respectively.

Next, at S815, an organ residence time is determined for each organ based on the curve determined at S810 for the organ. Also determined at S815 is an organ residence time uncertainty for each organ based on the uptake statistics uncertainties at each timepoint. Returning to FIG. 9, the organ residence time may be determined as the area under curve 920 and bound by vertical lines 950 and 960. Similarly, the organ residence time uncertainty may be determined as the area between curves 930 and 940 and bound by vertical lines 950 and 960.

Based on the organ residence time and the organ residence time uncertainty determined for each organ, an organ dose and organ dose uncertainty are determined for each organ at S820. According to some embodiments, an S_Value (mGy/MBq) for each organ is precomputed using a phantom and is applied directly to the determined organ residence time and the organ residence time uncertainty to determine the organ dose and organ dose uncertainty.

A dose kernel computation may also be used at S820 to determine the organ dose and organ dose uncertainty for each organ. This determination includes computation of residence time at the voxel level and filtering the resulting residence time image with a tissue-appropriate dose kernel to result in a dose distribution image.

Each functional component described herein may be implemented at least in part in computer hardware, in program code and/or in one or more computing systems executing such program code as is known in the art. Such a computing system may include one or more processing units which execute processor-executable program code stored in a memory system.

The foregoing diagrams represent logical architectures for describing processes according to some embodiments, and actual implementations may include more or different components arranged in other manners. Other topologies may be used in conjunction with other embodiments. Moreover, each component or device described herein may be implemented by any number of devices in communication via any number of other public and/or private networks. Two or more of such computing devices may be located remote from one another and may communicate with one another via any known manner of network(s) and/or a dedicated connection. Each component or device may comprise any number of hardware and/or software elements suitable to provide the functions described herein as well as any other functions. For example, any computing device used in an implementation of a system according to some embodiments may include a processor to execute program code such that the computing device operates as described herein.

All systems and processes discussed herein may be embodied in program code stored on one or more non-transitory computer-readable media. Such media may include, for example, a hard disk, a DVD-ROM, a Flash drive, magnetic tape, and solid state Random Access Memory (RAM) or Read Only Memory (ROM) storage units. Embodiments are therefore not limited to any specific combination of hardware and software.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
a nuclear imaging scanner to acquire a set of tomographic images of a patient volume associated with each of a plurality of timepoints of a first radiopharmaceutical therapy cycle;
a processing system to:
for each of the plurality of timepoints, determine a systematic uncertainty for each of a plurality of regions within the patient volume based on the set of tomographic images associated with the timepoint;
for each of the plurality of timepoints, determine a quantitative statistical uncertainty based on the set of tomographic images associated with the timepoint; and
determine a dose and a dose uncertainty for each of the plurality of regions based on the set of tomographic images, the systematic uncertainty and the quantitative statistical uncertainty for each of the plurality of timepoints; and
a display to present a cumulative dose and cumulative dose uncertainty for each of the plurality of regions based on the dose and the dose uncertainty determined for each of the plurality of regions.

2. A system according to claim 1, the nuclear imaging scanner to acquire a second set of tomographic images of the patient volume associated with each of a plurality of second timepoints of a second radiopharmaceutical therapy cycle; and
the processing system to:
for each of the plurality of second timepoints, determine a systematic uncertainty for each of the plurality of regions within the patient volume based on the second set of tomographic images associated with the second timepoint;
for each of the plurality of second timepoints, determine a quantitative statistical uncertainty based on the second set of tomographic images associated with the second timepoint; and
determine a second dose and a second dose uncertainty for each of the plurality of regions based on the second set of tomographic images, the systematic uncertainty and the quantitative statistical uncertainty for each of the plurality of second timepoints,
wherein the displayed cumulative dose and cumulative dose uncertainty is based on the dose, the dose uncertainty, the second dose and the second dose uncertainty.

3. A system according to claim 1, wherein determination of the dose for each region comprises, for each region:
determination of uptake statistics for each timepoint;
determination of a curve based on the determined uptake statistics;
determination of a region residence time based on the curve; and
determination of the dose based on the region residence time.

4. A system according to claim 3, wherein determination of systematic uncertainty for a first timepoint of the plurality of timepoints comprises:
generation of a first reconstructed image based on the set of tomographic images associated with the first timepoint;
determination of regional uptake statistics based on the first reconstructed image;
determination of a second reconstructed image based on the regional uptake statistics;
determination of a second set of tomographic images associated with the first timepoint based on the second reconstructed image;
generation of a third reconstructed image based on the second set of tomographic images; and
determination of the systematic uncertainty due to a partial volume effect for the first timepoint based on the first reconstructed image and the third reconstructed image.

5. A system according to claim 4, wherein determination of quantitative statistical uncertainty for the first timepoint of the plurality of timepoints comprises:
generation of a plurality of realizations of the set of tomographic images associated with the first timepoint;
generation of a plurality of reconstructed images of the patient volume based on respective ones of the plurality of realizations; and
determination of the quantitative statistical uncertainty for the first timepoint based on the plurality of reconstructed images.

6. A system according to claim 1, wherein determination of systematic uncertainty for a first timepoint of the plurality of timepoints comprises:
generation of a first reconstructed image based on the set of tomographic images associated with the first timepoint;
determination of regional uptake statistics based on the first reconstructed image;
determination of a second reconstructed image based on the regional uptake statistics;
determination of a second set of tomographic images associated with the first timepoint based on the second reconstructed image;
generation of a third reconstructed image based on the second set of tomographic images; and
determination of the systematic uncertainty due to a partial volume effect for the first timepoint based on the first reconstructed image and the third reconstructed image.

7. A system according to claim 6, the nuclear imaging scanner to acquire a second set of tomographic images of the patient volume associated with each of a plurality of second timepoints of a second radiopharmaceutical therapy cycle; and
the processing system to:
for each of the plurality of second timepoints, determine a systematic uncertainty for each of the plurality of regions within the patient volume based on the second set of tomographic images associated with the second timepoint;
for each of the plurality of second timepoints, determine a quantitative statistical uncertainty based on the second set of tomographic images associated with the second timepoint; and
determine a second dose and a second dose uncertainty for each of the plurality of regions based on the second set of tomographic images, the systematic uncertainty and the quantitative statistical uncertainty for each of the plurality of second timepoints,
wherein the displayed cumulative dose and cumulative dose uncertainty is based on the dose, the dose uncertainty, the second dose and the second dose uncertainty.

8. A method comprising:
acquiring a set of tomographic images of a patient volume associated with each of a plurality of timepoints of a first radiopharmaceutical therapy cycle;

for each of the plurality of timepoints, determining a systematic uncertainty for each of a plurality of regions within the patient volume based on the set of tomographic images associated with the timepoint;

for each of the plurality of timepoints, determining a quantitative statistical uncertainty based on the set of tomographic images associated with the timepoint;

determining a dose and a dose uncertainty for each of the plurality of regions based on the set of tomographic images, the systematic uncertainty and the quantitative statistical uncertainty for each of the plurality of timepoints; and displaying a cumulative dose and cumulative dose uncertainty for each of the plurality of regions based on the dose and the dose uncertainty determined for each of the plurality of regions.

9. A method according to claim 8, further comprising:

acquiring a second set of tomographic images of the patient volume associated with each of a plurality of second timepoints of a second radiopharmaceutical therapy cycle;

for each of the plurality of second timepoints, determining a systematic uncertainty for each of the plurality of regions within the patient volume based on the second set of tomographic images associated with the second timepoint;

for each of the plurality of second timepoints, determining a quantitative statistical uncertainty based on the second set of tomographic images associated with the second timepoint; and determining a second dose and a second dose uncertainty for each of the plurality of regions based on the second set of tomographic images, the systematic uncertainty and the quantitative statistical uncertainty for each of the plurality of second timepoints, wherein the displayed cumulative dose and cumulative dose uncertainty is based on the dose, the dose uncertainty, the second dose and the second dose uncertainty.

10. A method according to claim 8, wherein determining the dose for each region comprises, for each region:

determining uptake statistics for each timepoint;

determining a curve based on the determined uptake statistics;

determining a region residence time based on the curve; and determining the dose based on the region residence time.

11. A method according to claim 10, wherein determining systematic uncertainty for a first timepoint of the plurality of timepoints comprises:

generating a first reconstructed image based on the set of tomographic images associated with the first timepoint;

determining regional uptake statistics based on the first reconstructed image;

determining a second reconstructed image based on the regional uptake statistics;

determining a second set of tomographic images associated with the first timepoint based on the second reconstructed image;

generating a third reconstructed image based on the second set of tomographic images; and determining the systematic uncertainty due to a partial volume effect for the first timepoint based on the first reconstructed image and the third reconstructed image.

12. A method according to claim 11, wherein determining quantitative statistical uncertainty for the first timepoint of the plurality of timepoints comprises:

generating a plurality of realizations of the set of tomographic images associated with the first timepoint;

generating a plurality of reconstructed images of the patient volume based on respective ones of the plurality of realizations; and determining the quantitative statistical uncertainty for the first timepoint based on the plurality of reconstructed images.

13. A method according to claim 8, wherein determining systematic uncertainty for a first timepoint of the plurality of timepoints comprises:

generating a first reconstructed image based on the set of tomographic images associated with the first timepoint;

determining regional uptake statistics based on the first reconstructed image;

determining a second reconstructed image based on the regional uptake statistics;

determining a second set of tomographic images associated with the first timepoint based on the second reconstructed image;

generating a third reconstructed image based on the second set of tomographic images; and determining the systematic uncertainty for the first timepoint based on the first reconstructed image and the third reconstructed image.

14. A method according to claim 13, further comprising:

acquiring a second set of tomographic images of the patient volume associated with each of a plurality of second timepoints of a second radiopharmaceutical therapy cycle; and for each of the plurality of second timepoints, determining a systematic uncertainty for each of the plurality of regions within the patient volume based on the second set of tomographic images associated with the second timepoint;

for each of the plurality of second timepoints, determining a quantitative statistical uncertainty based on the second set of tomographic images associated with the second timepoint; and determining a second dose and a second dose uncertainty for each of the plurality of regions based on the second set of tomographic images, the systematic uncertainty and the quantitative statistical uncertainty for each of the plurality of second timepoints, wherein the displayed cumulative dose and cumulative dose uncertainty is based on the dose, the dose uncertainty, the second dose and the second dose uncertainty.

15. A computing system comprising:

a storage device storing a set of tomographic images of a patient volume associated with each of a plurality of timepoints of a first radiopharmaceutical therapy cycle, and processor-executable process steps;

a processor to execute the processor-executable process steps to cause the computing system to:

determine an amount of a first type of uncertainty for each of the plurality of timepoints and for each of a plurality of regions within the patient volume based on the set of tomographic images associated with the timepoint;

determine an amount of a second type of uncertainty for each of the plurality of timepoints based on the set of tomographic images associated with the timepoint; and determining a dose and a dose uncertainty for each of the plurality of regions based on the set of tomographic images, the amount of the first type of uncertainty and the amount of the second type of uncertainty for each of the plurality of timepoints; and a display to display a cumulative dose and cumulative dose uncertainty for each of the plurality of regions based on the dose and the dose uncertainty determined for each of the plurality of regions.

16. A system according to claim 15, the storage device storing a second set of tomographic images of the patient volume associated with each of a plurality of second timepoints of a second radiopharmaceutical therapy cycle, and the processor to execute the processor-executable process steps to cause the computing system to:

determining a second amount of the first type of uncertainty for each of the plurality of second timepoints and for each of the plurality of regions within the patient volume based on the second set of tomographic images associated with the second timepoint;

determining a second amount of the second type of uncertainty for each of the plurality of second timepoints based on the second set of tomographic images associated with the second timepoint; and determining a second dose and a second dose uncertainty for each of the plurality of regions based on the second set of tomographic images, the second amount of the first type of uncertainty and the second amount of the second type of uncertainty for each of the plurality of second timepoints, wherein the displayed cumulative dose and cumulative dose uncertainty is based on the dose, the dose uncertainty, the second dose and the second dose uncertainty.

17. A system according to claim 15, wherein determination of the dose for each region comprises, for each region:

determination of uptake statistics for each timepoint;
determination of a curve based on the determined uptake statistics;
determination of a region residence time based on the curve; and
determination of the dose based on the region residence time.

18. A system according to claim 17, wherein determination of the amount of the first type of uncertainty for a first timepoint of the plurality of timepoints comprises:

generation of a first reconstructed image based on the set of tomographic images associated with the first timepoint;
determination of regional uptake statistics based on the first reconstructed image;
determination of a second reconstructed image based on the regional uptake statistics;
determination of a second set of tomographic images associated with the first timepoint based on the second reconstructed image;
generation of a third reconstructed image based on the second set of tomographic images; and
determination of the amount of the first type of uncertainty for the first timepoint based on the first reconstructed image and the third reconstructed image.

19. A system according to claim 18, wherein determination of the amount of the second type of uncertainty for the first timepoint of the plurality of timepoints comprises:

generation of a plurality of realizations of the set of tomographic images associated with the first timepoint;
generation of a plurality of reconstructed images of the patient volume based on respective ones of the plurality of realizations; and
determination of the amount of the second type of uncertainty for the first timepoint based on the plurality of reconstructed images.

20. A method according to claim 15, wherein determination of the amount of the first type of uncertainty for a first timepoint of the plurality of timepoints comprises:

generation of a first reconstructed image based on the set of tomographic images associated with the first timepoint;
determination of regional uptake statistics based on the first reconstructed image;
determination of a second reconstructed image based on the regional uptake statistics;
determination of a second set of tomographic images associated with the first timepoint based on the second reconstructed image;
generation of a third reconstructed image based on the second set of tomographic images; and
determination of the amount of the first type of uncertainty for the first timepoint based on the first reconstructed image and the third reconstructed image.

* * * * *